US007888528B2

(12) United States Patent
Afzali-Ardakani et al.

(10) Patent No.: US 7,888,528 B2
(45) Date of Patent: Feb. 15, 2011

(54) PHOTOSENSITIVE SELF-ASSEMBLED MONOLAYER FOR SELECTIVE PLACEMENT OF HYDROPHILIC STRUCTURES

(75) Inventors: Ali Afzali-Ardakani, Ossining, NY (US); Teresita O. Graham, Irvington, NY (US); James B. Hannon, Mahopac, NY (US); George S. Tulevski, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/538,119

(22) Filed: Aug. 8, 2009

(65) Prior Publication Data

US 2010/0003616 A1  Jan. 7, 2010

Related U.S. Application Data

(62) Division of application No. 11/870,167, filed on Oct. 10, 2007, now Pat. No. 7,732,119.

(51) Int. Cl.
 *C07F 9/38* (2006.01)
 *C07C 205/06* (2006.01)
 *G03F 7/004* (2006.01)
 *G03F 7/00* (2006.01)

(52) U.S. Cl. .............................. 562/15; 562/8; 562/400; 562/405; 562/435; 430/270.1

(58) Field of Classification Search .............. 430/270.1, 430/322, 311; 428/195.1; 562/8, 15, 400, 562/405, 435
 See application file for complete search history.

(56) References Cited

U.S. PATENT DOCUMENTS

| 5,620,850 | A | 4/1997 | Bamdad et al. |
| 7,332,264 | B2 | 2/2008 | Doshi et al. |
| 2005/0214195 | A1 | 9/2005 | Jung et al. |
| 2005/0233473 | A1 | 10/2005 | Cicero et al. |
| 2005/0245739 | A1 | 11/2005 | Fukushima et al. |
| 2007/0000866 | A1 | 1/2007 | Ryan et al. |

OTHER PUBLICATIONS

Shirahata et al., Thin Solid Films 499 (2006), 293-298.
Bardecker et al., Directed Assembly of Single-Walled Carbon Nanotubes via Drop-Casting onto a UV-Patterned Photosensitive Monolayer, Journal of the American Chemical Society, 2008, 130(23), pp. 7226-7227.

*Primary Examiner*—Amanda C. Walke
(74) *Attorney, Agent, or Firm*—Scully, Scott, Murphy & Presser, P.C.; Vazken Alexanian (57) ABSTRACT

A photosensitive monolayer is self-assembled on an oxide surface. The chemical compound of the photosensitive monolayer has three components. A first end group provides covalent bonds with the oxide surface for self assembly on the oxide surface. A photosensitive group that dissociates upon exposure to ultraviolet radiation is linked to the first end group. A second end group linked to the photosensitive group provides hydrophobicity. Upon exposure to the ultraviolet radiation, the dissociated photosensitive group is cleaved and forms a hydrophilic derivative in the exposed region, rendering the exposed region hydrophilic. Carbon nanotubes or nanocrystals applied in an aqueous dispersion are selectively attracted to the hydrophilic exposed region to from electrostatic bonding with the hydrophilic surface of the cleaved photosensitive group.

2 Claims, 10 Drawing Sheets

PHOTOSENSITIVE SELF-ASSEMBLED MONOLAYER FOR SELECTIVE PLACEMENT OF HYDROPHILIC STRUCTURES

CROSS-REFERENCE TO RELATED APPLICATIONS

This application is a divisional of U.S. patent application Ser. No. 11/870,167, filed Oct. 10, 2007.

The present invention was made with U.S. Government support under Contract No. N66001-06-C-2047 awarded by Defense Advanced Research Projects Agency (DARPA).

BACKGROUND

The present invention generally relates to methods forming a patterned surface containing a hydrophobic region and a hydrophilic region, methods of selective placement of carbon nanotube and a nanocrystal on the patterned surface, photosensitive compounds for forming such a pattern, and structures containing a self-aligned carbon nanotube or a nanocrystal.

With the realization that end of scaling for conventional CMOS integrated circuits is fast approaching in the semiconductor industry, alternative nanostructures and materials have been investigated. Of such nanostructures and materials, carbon nanotubes (CNTs) offer excellent intrinsic properties that are suitable for high performance nanoscale devices. Research in the replacement of semiconductor based field effect transistors and optoelectronic devices and sensors with carbon nanotube based nanoscale devices has been producing promising results in this field.

A key advantage of CNTs over conventional CMOS devices is that scaling limitations of MOSFETs due to boundary scattering of electrons from imperfect interfaces are solved naturally in CNTs which have a smooth, well coordinated graphene structure with no bonds to the outside. This enables CNTs to retain excellent transport properties to much smaller lateral dimensions than silicon. The small radius and possibility of completely surrounding the CNT by a gate provide excellent electrostatic confinement of channel electrons, enabling the channel length to be scaled down to very small dimensions, and their small size would enable high packing densities.

Although single, isolated CNT based field effect transistors and other devices have been demonstrated, many challenges remain in the construction of an integrated circuit employing CNTs as an active material. One such challenge is reliable placement of CNTs on a substrate surface with alignment, i.e., placement of the CNTs in a predefined region for fabrication of a CNT based device.

Several methods for selective placement of CNTs on a surface have been disclosed in the prior art. An exemplary prior art method employs the steps of:

prepatterning the surface into a metal oxide region and a silicon oxide region;

applying alkylphosphonic acids or alkylhydroxamic acids on the prepatterned surface, wherein the alkylphosphonic acids or alkylhydroxamic acids self-assemble on the silicon oxide region, while not assembling on the metal oxide region; and applying functionalized CNTs on the prepatterned surface containing the patterned alkylphosphonic acids or alkylhydroxamic acids, wherein the functionalized CNTs are selectively attracted to the metal oxide region.

The exemplary prior art method has the drawback of requiring at least one lithographic step for formation of the metal oxide region and the silicon oxide region, in which a photoresist needs to be applied directly on the surface to be patterned, thus making the cleaning of residual photoresist material from the surface difficult and thereby degrading the effectiveness and fidelity of the pattern to be formed on the surface.

In view of the above, there exists a need for a method for patterning a surface into hydrophobic regions and hydrophilic regions without direct contact of a photoresist with the surface so that residual material from the photoresist does not produce adverse effects on the pattern, and a chemical compound for effecting such a method.

BRIEF SUMMARY

The present invention addresses the needs described above by providing a method for patterning a surface into hydrophobic regions and hydrophilic regions without direct contact of a photoresist with the surface, and a chemical compound for effecting such a method.

A photosensitive monolayer is self-assembled on an oxide surface, which may be a metal oxide surface or a semiconductor oxide surface. The oxide surface may, or may not be, patterned. The chemical compound of the photosensitive monolayer has three components. A first end group provides covalent bonds with the oxide surface for self assembly on the oxide surface. A photosensitive group that dissociates upon exposure to ultraviolet radiation is linked to the first end group. A second end group linked to the photosensitive group provides hydrophobicity. The self-assembled monolayer of the photosensitive compound is initially hydrophobic without ultraviolet radiation. Upon exposure to ultraviolet radiation, the dissociated photosensitive group is cleaved and forms a hydrophilic derivative in the exposed region, rendering the exposed region hydrophilic. Carbon nanotubes applied in an aqueous dispersion are selectively attracted to the hydrophilic exposed region to from electrostatic bonding with the hydrophilic surface of the cleaved photosensitive group, enabling patterning of the carbon nanotubes without direct contact of a photoresist with the oxide surface. Hydrophilic nanocrystals may also be patterned in the same manner.

According to an aspect of the present invention, a structure is provided, which comprises a patterned monolayer located on an oxide surface of a substrate;

wherein the patterned monolayer contains a first contiguous region of a first material and a second contiguous region of a second material, and wherein the first contiguous region and the second contiguous region laterally abut, and do not overlie, each other;

and wherein the first material includes:

a first end group that forms covalent bonds with the oxide surface;

a photosensitive group that dissociates upon exposure to ultraviolet radiation linked to the first end group; and a second end group having hydrophobicity and linked to the photosensitive group; and wherein the second material includes:

said first end group; and a third end group linked to the first end group and having hydrophilicity and derived from the photosensitive group by dissociation of a link by ultraviolet radiation.

In one embodiment, the structure comprises at least one carbon nanotube located directly on the second contiguous region and not overlying the first contiguous region.

In another embodiment, the structure further comprises at least one nanocrystal located directly on the second contiguous region and not overlying the first contiguous region. The nanocrystal may be a metal nanocrystals such as gold or palladium or a semiconducting nanocrystal or an oxide nanocrystal.

In even another embodiment, the first end group comprises one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

In yet another embodiment, the oxide is a metal oxide, wherein the metal is selected from elemental metals and an alloy thereof.

In still another embodiment, the oxide is a compound of a semiconductor material and oxygen, and wherein the semiconductor material is one of silicon, germanium, carbon, and an alloy thereof.

According to another aspect of the present invention, a photosensitive compound is provided, which comprises:

a first end group that forms covalent bonds with the oxide surface;

a photosensitive group that dissociates upon exposure to ultraviolet radiation linked to the first end group; and a second end group having hydrophobicity and linked to the photosensitive group.

In one embodiment, the photosensitive compound forms a self-assembled monolayer on a metal oxide.

In another embodiment, the assembled monolayer of the photosensitive compound transforms, upon irradiation with ultraviolet light, into a monolayer having a carboxylic acid end group.

According to yet another aspect of the present invention, a method of manufacturing a structure is provided, which comprises:

providing a substrate containing an oxide surface;

applying a monolayer of a photosensitive material to said oxide surface; wherein the photosensitive material includes:

a first end group that forms covalent bonds with the oxide surface;

a photosensitive group that dissociates upon exposure to ultraviolet radiation linked to the first end group; and a second end group having hydrophobicity and linked to the photosensitive group; and lithographically exposing a region of the monolayer to ultraviolet radiation, wherein the photosensitive group in the exposed region dissociates upon exposure to said ultraviolet radiation and forms a third end group rendering the surface hydrophilic.

In one embodiment, the exposed region laterally abuts, and does not overlie, an unexposed region of the monolayer, and wherein the unexposed region is not exposed to the ultraviolet radiation, and wherein the exposed region and the unexposed region collective constitute a pattern of a hydrophibic surface and a hydrophilic surface.

In another embodiment, the method further comprises selectively placing at least one carbon nanotube or at least one nanocrystal on the pattern, wherein the at least one carbon nanotube is preferentially placed over the exposed region.

In even another embodiment, the at least one carbon nanotube or the at least one nanocrystal is deposited from organic solvents or aqueous solutions containing surfactants.

In yet another embodiment, the at least one carbon nanotube is functionalized with acid-terminating functionality or amine-terminating functionality and is deposited from an aqueous solution or an aqueous alcohol solution.

In still yet another embodiment, the nanocrystal is a gold nanocrystal, a palladium nanocrystal, or a semiconducting nanocrystal.

BRIEF DESCRIPTION OF THE SEVERAL VIEWS OF THE DRAWINGS

FIGS. 1-4B are sequential vertical cross-sectional views of an exemplary structure employing a monolayer of a photosensitive material for patterning a hydrophobic surface and a hydrophilic surface.

DETAILED DESCRIPTION

As stated above, the present invention relates to methods forming a patterned surface containing a hydrophobic region and a hydrophilic region, methods of self-alignment of a carbon nanotube and a nanocrystal on the patterned surface, photosensitive compounds for forming such a pattern, and structures containing a self-aligned carbon nanotube or a nanocrystal. It is noted that like and corresponding elements are referred to by like reference numerals.

The following terms are employed herein:

As defined herein, the term "alkyl", alone or in combination with any other term, refers to a straight-chain or branch-chain saturated aliphatic hydrocarbon radical containing a number of carbon atoms from 1 to 20, preferably from 1 to 10 and more preferably from 1 to 5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

As defined herein, the term "alkoxy", alone or in combination with any other term, refers to —O-alkyl, wherein alkyl is as defined above.

As defined herein, the term "alkylthio," alone or in combination with any other term, refers to —S-alkyl, wherein alkyl is as defined above.

Figure 1:
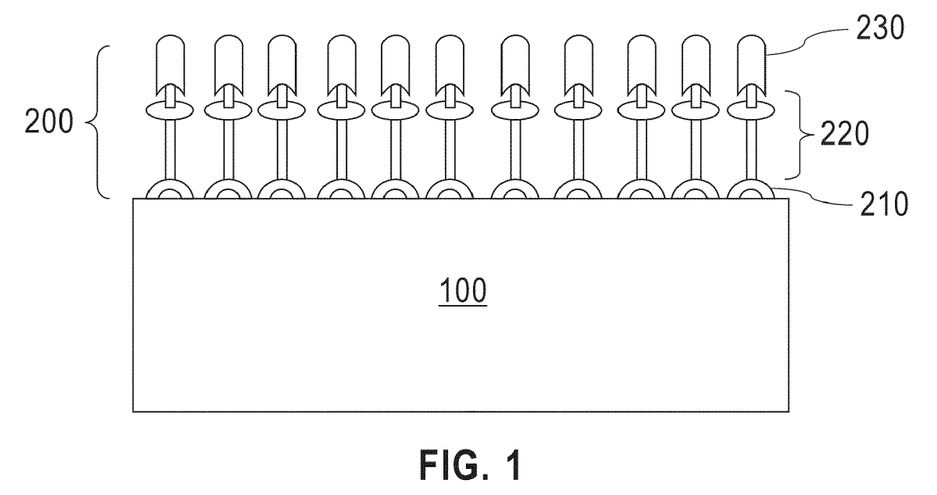

Referring to FIG. 1, an exemplary structure according to the present invention comprises a substrate 100 and a monolayer 200 of a photosensitive material. The substrate 100 may comprise an insulator material, a semiconductor material, or a metallic material. The top surface of the insulator material which contacts the monolayer 200 of the photosensitive material comprises an oxide surface which may contain a metal oxide or a semiconductor oxide. The metal oxide contains at least one elemental metal. The semiconductor oxide is a compound of a semiconductor material and oxygen, and wherein the semiconductor material is one of silicon, germanium, carbon, and an alloy thereof.

The monolayer 200 of the photosensitive material is attached to the oxide surface by covalent bonds. The photosensitive material comprises three groups. A first end group 210 forms covalent bonds with the oxide surface which contains the at least one elemental metal in the case of the metal oxide or the semiconductor material such as silicon in the case of the semiconductor oxide. The first end group 210 may comprise a carboxylic acid, a phosphonic acid or, a hydroxamic acid. The photosensitive group 220 is linked to the first end group. The photosensitive group 220 dissociates upon exposure to ultraviolet radiation. The photosensitive group 220 may comprise a nitribenzyl moiety having a photosensitive bond such as a CO—O—CH$_2$ bond or a CH$_2$—NH—CO bond. A second end group 230 is linked to the photosensitive group 220 and provides hydrophobicity to the photosensitive material. The second end group 230 may comprise one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

The covalent bonds between the first end group 210 in each molecule of the photosensitive compound and the oxide surface enables self-assembly of the photosensitive material on the oxide surface as the monolayer 200. This is because the covalent bond is formed only between the acidic end group of photosensitive material and the oxide surface. In other words, the molecules of the photosensitive material does not provide atom available for covalent bonding except for those that are bonded to the oxide surface.

Figure 2:
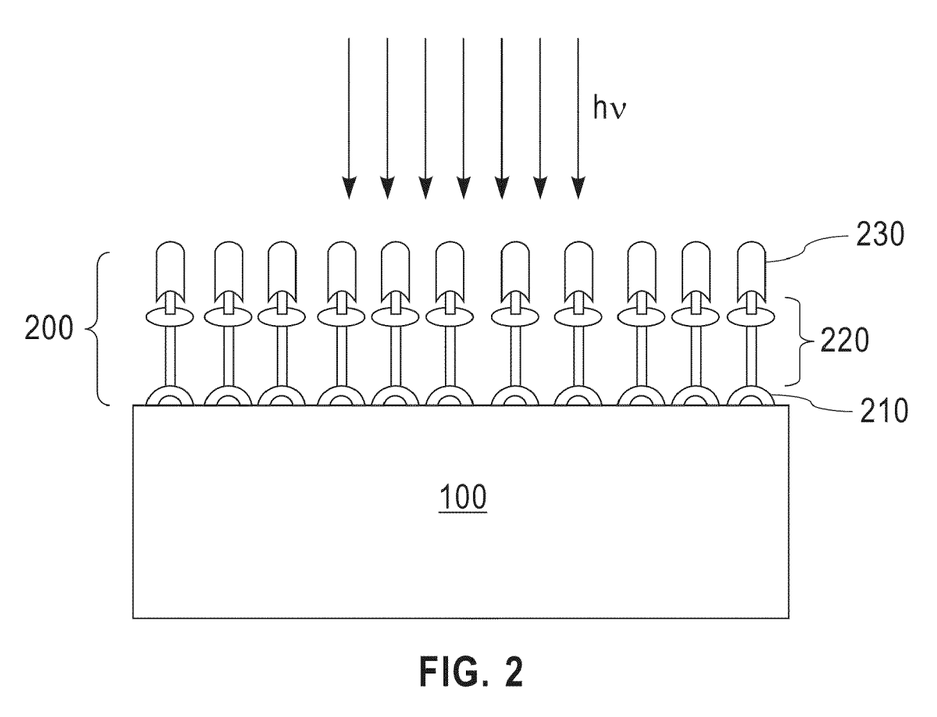

Referring to FIG. 2, the exemplary structure is subjected to a patterned beam of ultraviolet radiation. A conventional lithography tool and a conventional lithographic mask may be employed to generate the patterned beam of ultraviolet radiation. Application of a photoresist onto the substrate 100 is not necessary since the monolayer 200 of the photosensitive material reacts with the patterned beam of ultraviolet radiation.

The photons of the patterned beam of ultraviolet radiation react with the photosensitive group 220 to dissociate the photosensitive group 220 within the exposed region of the monolayer 200 of the photosensitive material. As the photosensitive group 220 dissociates by the ultraviolet radiation, the second end group 230 having hydrophobicity is removed along with some atoms of the photosensitive group 220. The remaining portion of the photosensitive group 220 forms a derivative of the photosensitive group 220 having an exposed hydrophilic functionality. After removal of the cleaved portion containing the second end group 230, for example, in an aqueous or aqueous alcohol solution, the exposed portion of the monolayer 200 containing the exposed photosensitive material has a hydrophilic surface.

Figure 3:
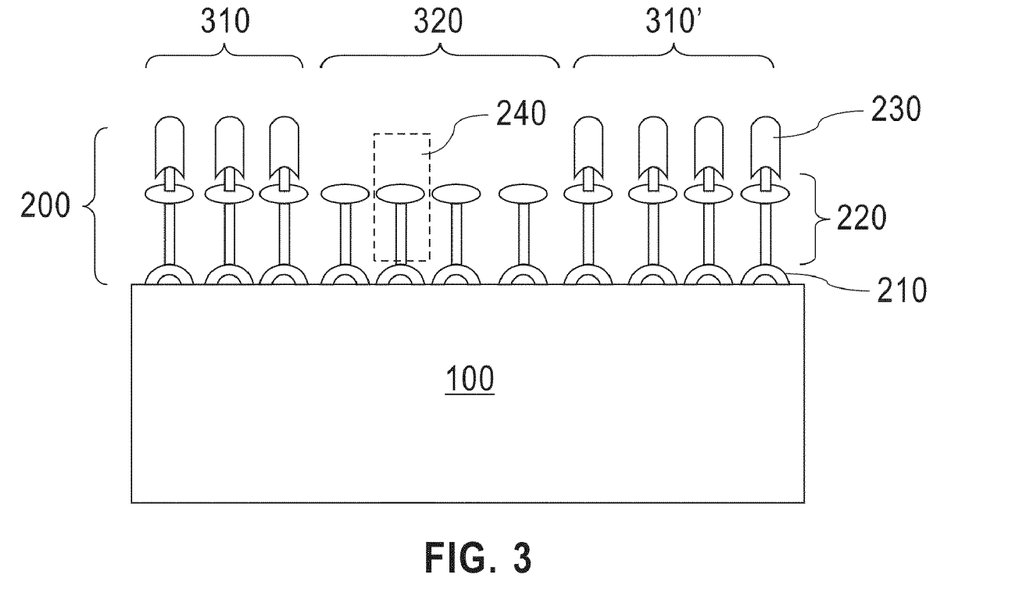

Referring to FIG. 3, the monolayer 200 is thus patterned and contains at least a first contiguous region 310 and at least a second contiguous region 320. The monolayer 200 may contain another first contiguous region 310' and/or another second contiguous region (not shown). Typically, the monolayer 200 constitutes a plurality of first contiguous regions (310, 310') and a plurality of second contiguous regions 320, each containing a plurality of molecules. Since the monolayer 200 contains a single layer of material, the first contiguous region 310 and the second contiguous region 320 laterally abut, and do not overlie, each other. The first contiguous region 310 comprises the photosensitive material. The second contiguous region 320 has a lithographic dimension and comprises a derivative of the photosensitive material. The derivative of the photosensitive material comprises:

the first end group 210; and a third end group 240 linked to the first end group 210 and having hydrophilicity and derived from the photosensitive group 220 by dissociation of a link by ultraviolet radiation.

Figure 4A:
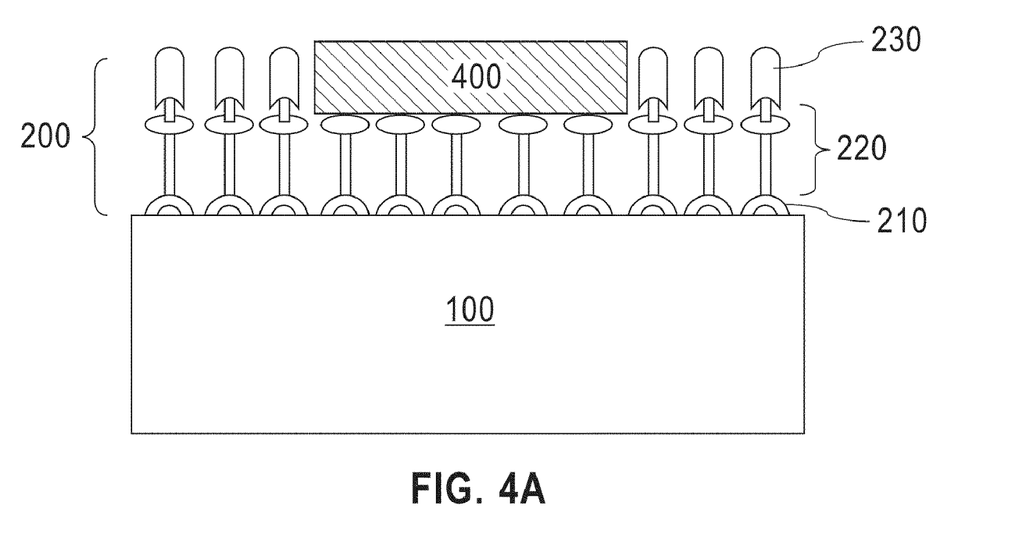

Referring to FIG. 4A, at least one carbon nanotube 400 is preferentially placed on the second contiguous region 320 (See FIG. 3) of the monolayer 200. Carbon nanotubes are applied to the surfaces of the monolayer 200 as a dispersion of carbon nanotubes in an organic solvent or an aqueous solution. Since the first contiguous regions (310, 310'; See FIG. 3) has a hydrophobic surface and the second contiguous region 320 has a hydrophilic surface, the carbon nanotubes are repulsed from the second contiguous region 320 and attracted to the first contiguous regions (310, 310'). Thus, the placement of the at least one carbon nanotube 400 on the substrate 100 may be patterned without employing a conventional photoresist that contacts the substrate 100.

Figure 4B:
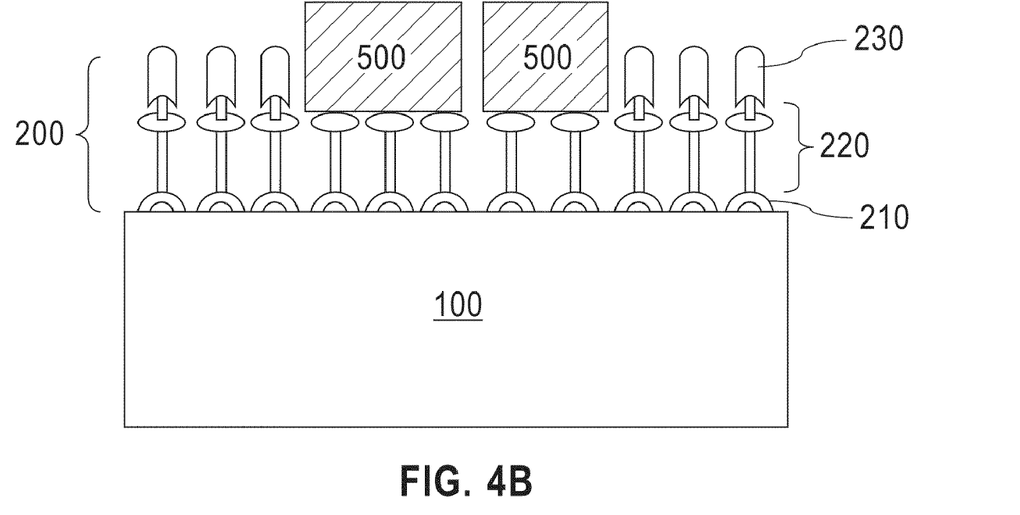

Referring to FIG. 4B, the exemplary structure in FIG. 3 may alternately be employed for self-assembly of nanocrystals 500 containing hydrophilic surfaces. The nanocrystals 500 may have dimensions from about 1 nm to about 100 nm. The nanocrystals 500 that may be patterned in this manner include, but are not limited to, a gold nanocrystal, a palladium nanocrystal, or a semiconducting nanocrystal. As in the case of the carbon nanotubes, the nanocrystals 500 are repulsed from the second contiguous region 320 and attracted to the first contiguous regions (310, 310'). Thus, the placement of the nanocrystals 500 on the substrate 100 may be patterned without employing a conventional photoresist that contacts the substrate 100.

The following are two embodiments of synthesizing the photosensitive material employed to form the monolayer 200, which do not limit the scope of the present invention.

Embodiment 1

Synthesis of Photosensitive Phosphonic Acids

Figure 5A:
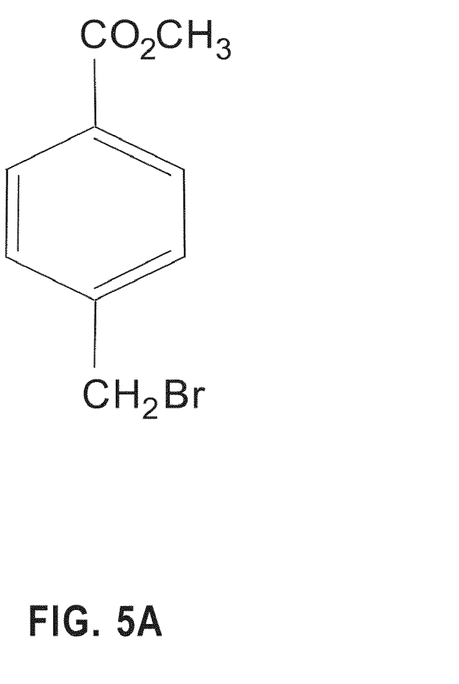
FIGS. 5A-5D are the chemical structures of compounds employed in the manufacture of 4-diethylphosphonatomethyl benzoic acid chloride, which is the compound of FIG. 5D according to a first embodiment of the present invention.
Figure 5B:
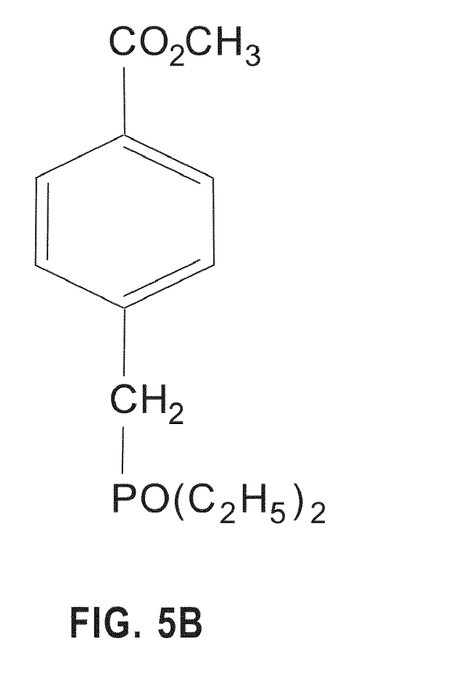

According to embodiment 1, or a first embodiment, of the present invention, a mixture of methyl 4-bromomethylbenzoate, of which the chemical formula is shown in FIG. 5A, and triethyl phosphate is formed and heated at an elevated temperature. For example, 10 grams of methyl 4-bromomethylbenzoate and 40 grams of triethyl phosphate may be mixed and heated at 120° C. for 4 hours. The solution is cooled and excess triethyl phosphite may be evaporated under reduced pressure to form a light yellow oil, which is methyl diethylphosphonatomathyl-benzoate, of which the chemical formula is shown in FIG. 5B. Methyl diethyl-phosphonatomathylbenzoate in the form of the light yellow oil may be used without further purification in the next step.

Figure 5C:
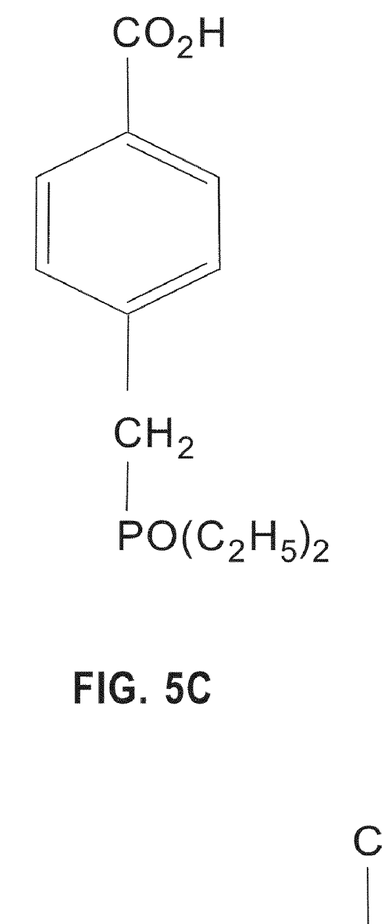

Methyl diethylphosphonatomathylbenzoate is then dissolved in methanol and lithium hydroxide is added to the solution. For example, 10 grams of methyl diethylphosphonatomathyl-benzoate may be dissolved in 50 ml of methanol and 40 ml of 5% lithium hydroxide may be added. The mixture is then stirred, for example, at room temperature for 5 hours. Methanol is then evaporated under reduced pressure and the aqueous solution is then made acidic by addition of dilute hydrochloric acid. The precipitate is filtered, washed with water, and then dried. Recrystallization from water produces white crystals of 4-diethylphosphonatomethyl benzoic acid, of which the chemical formula is shown in FIG. 5C.

Figure 5D:
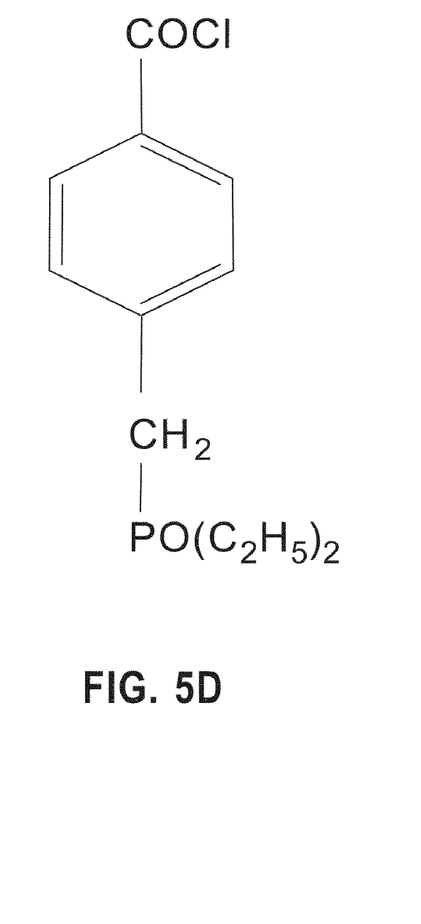
Figure 6:
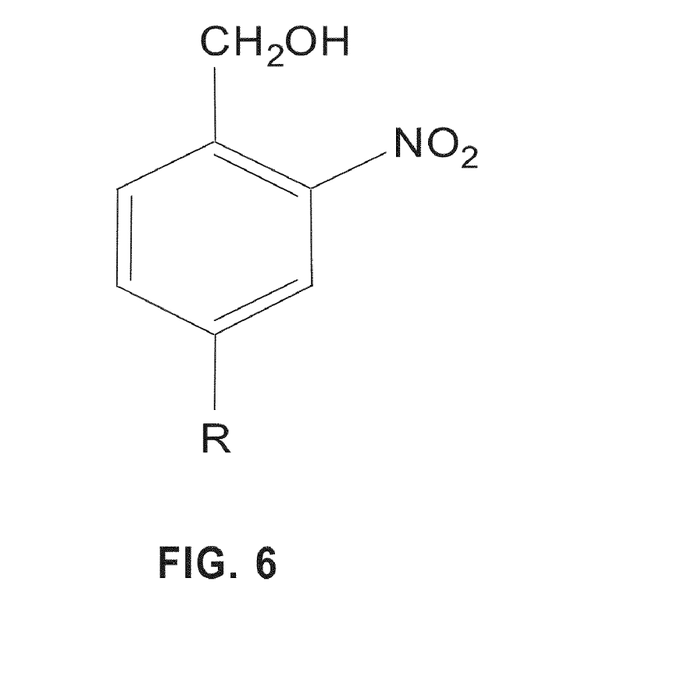
FIG. 6 is the chemical structure of 4-substituted 2-nitrobenzyl alcohol employed in the first embodiment of the present invention.

4-diethylphosphonatomethyl benzoic acid is then added to anhydrous dichloromethane. For example, 5.0 grams of 4-diethylphosphonatomethyl benzoic acid may be added to 50 ml of anhydrous dichloromethane. Excess amount of oxalyl chloride is added to this solution. A trace amount of N,N-dimethylformamide is then added to the solution. The mixture may be stirred, for example, under nitrogen for 4 hours. The solvent and the excess oxalyl chloride is then evaporated under reduce pressure to produce a colorless oil, which is 4-diethylphosphonato-methyl benzoic acid, of which the chemical formula is shown in FIG. 5D.

4-diethylphosphonato-methyl benzoic acid thus obtained in the form of the colorless oil is then dissolved in anhydrous dichloromethane. The solution is then added to a solution of 2-nitrobenzyl alcohol in dichloromethane containing triethylamine. The chemical structure for 2-nitrobenzyl alcohol is shown in FIG. 5. After stirring 4 hours at room temperature, the solution is washed with 5% sodium bicarbonate, dilute hydrochloric acid and brine successively, and then dried over anhydrous magnesium and filtered. The solvent is then evaporated under reduced pressure and solid residue is crystallized from ethanol to give a phosphonate ester. The ester is dissolved in anhydrous dichloromethane and treated with 4 equivalent of bromotrimethylsilane, and then stirred under nitrogen for 5 hours. Methanol and a few drops of hydrochloric acid is added and stirring may be continued for additional 1 hour. The precipitate is filtered and washed with ether, dried and crystallized from ethanol to form photosensitive phosphonic acid as white crystals.

Figure 7:
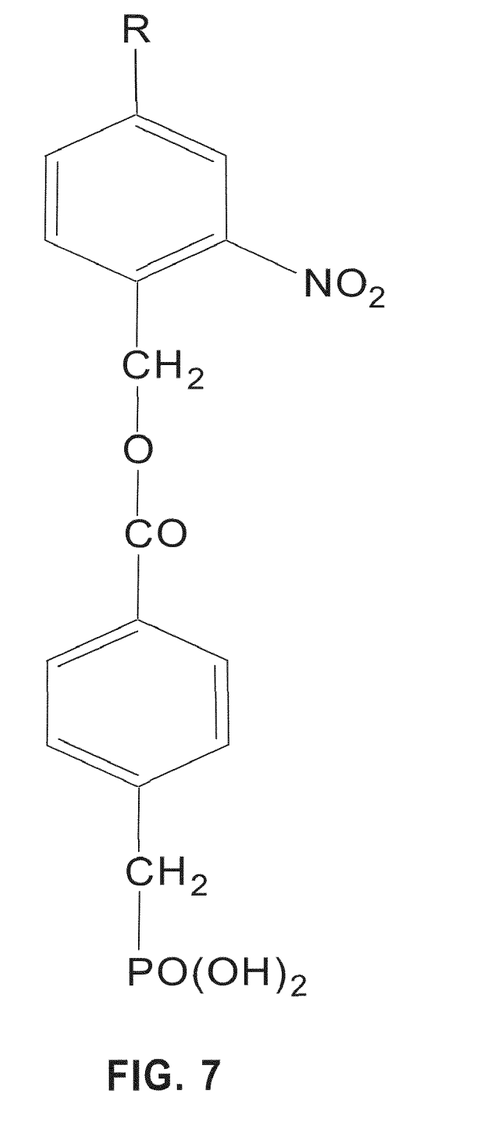
FIG. 7 is the chemical structure of the photosensitive phosphonic acid according to the first embodiment of the present invention.

The chemical structure of the photosensitive phosphonic acid is obtained from the chemical structure of FIG. 7 by replacement of R with a hydrogen atom, i.e., by substituting H- for R in FIG. 7.

The above procedure may be performed with the replacement of the 2-nitrobenzyl alcohol with 4-trifluoromethyl-2-nitrobenzyl alcohol. A 4-substituted photosensitive phosphonic acid, in which R in FIG. 7 is replaced with $CF_3$—, is obtained by this process. Purification of this compound may be performed through crystallization from ethanol.

Further, the above procedure may be performed with the replacement of the 2-nitrobenzyl alcohol with 4-hexadecyloxy-2-nitrobenzyl alcohol. Another 4-substituted photosensitive phosphonic acid, in which R in FIG. 7 is replaced with $C_{16}H_{33}O$—, is obtained by this process. Purification of this compound may be performed through crystallization from toluene-ethanol mixture.

In general, various alcohol may be employed to produce various photosensitive phosphonic acid. R may be one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

Figure 8:
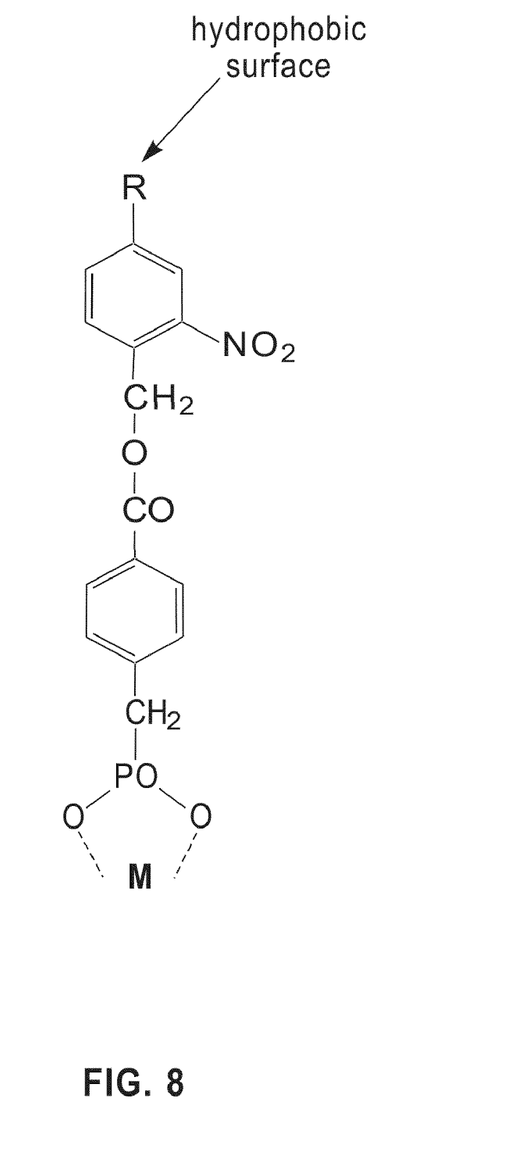
FIG. 8 is the chemical structure of the photosensitive phosphonic acid as attached to an oxide surface according to the first embodiment of the present invention.

Referring to FIG. 8, an unsubstituted or 4-substituted photosensitive phosphonic acid as covalently bonded to a metal M on the surface of a metal oxide is shown. Two oxygen atoms bond to the metal oxide and provide a hydrophobic surface as R is exposed on the outside of the monolayer 200 (See FIG. 1). The end group of the unsubstituted or 4-substituted photosensitive phosphonic acid is phosphonic acid has the formula $PO(OH)_2$. During bonding to the oxide surface, the end group loses two hydrogen atoms. Thus, two oxygen atoms form a covalent bond with the metal atom or the semiconductor atom of the oxide on the surface.

Figure 9:
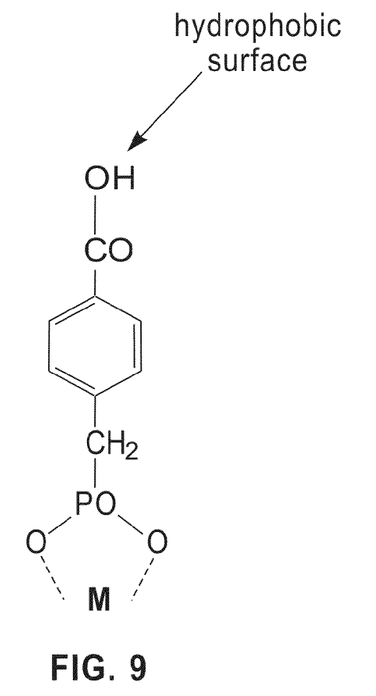
FIG. 9 is the chemical structure of a derivative of the photosensitive phosphonic acid upon exposure to ultraviolet radiation to form a hydrophilic surface and as attached to an oxide surface according to the first embodiment of the present invention.

Referring to FIG. 9, a derivative of the unsubstituted or 4-substituted photosensitive phosphonic acid after exposure to ultraviolet radiation is shown in which the CO—O—$CH_2$ bond in the photosensitive phosphonic acid is broken to provide a CO—OH termination, which provides hydrophilicity. Thus, the derivative of the unsubstituted or 4-substituted photosensitive phosphonic acid as covalently bonded to the metal M on the surface of the metal oxide provides a hydrophilic surface since —OH is exposed on the outside of the second contiguous region 320 of the monolayer 200.

Embodiment 2

Synthesis of Photosensitive Hydroxamic Acids

Figure 10A:
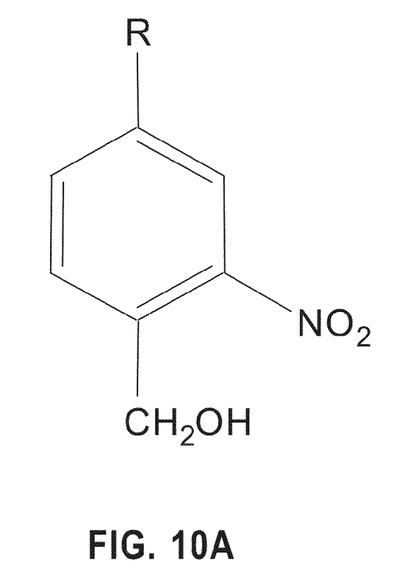
FIGS. 10A and 10B are the chemical structures of compounds employed in the manufacture of 4-substituted 2-nitrobenzyloxycarbonyl chloride, which is the compound of FIG. 10B according to a second embodiment of the present invention.
Figure 10B:
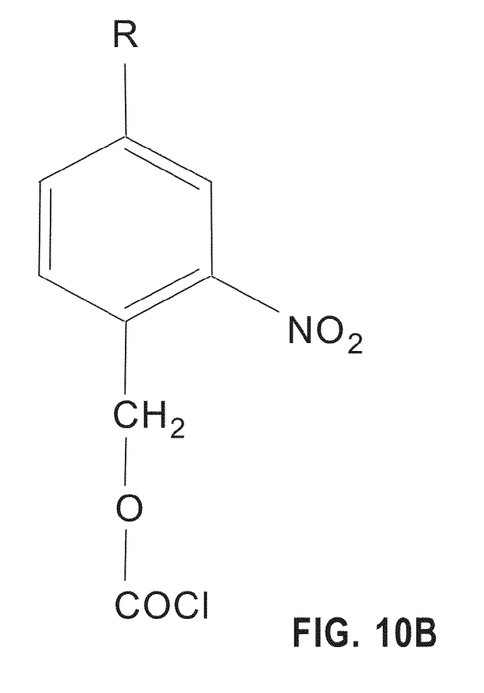

According to embodiment 2, or a second embodiment, of the present invention, 2-nitrobenzyl alcohol, of which the structural formula is shown in FIG. 10A, is added to a solution of phosgene. The solution of phosgene may be generated by heating a solution of diphosgene in tetrahydrofuran in the presence of activated charcoal. The mixture of 2-nitrobenzyl alcohol and the phosgene solution is stirred, for example, at room temperature for 4 hours. The solvent and excess phosgene is evaporated under reduced pressure and an oily residue is obtained, which is nitrobenzyloxycarbonyl chloride, of which the chemical formula is shown in FIG. 10B. The nitrobenzyloxycarbonyl chloride in the form of the oily residue is used without further purification in the next step.

Figure 11:
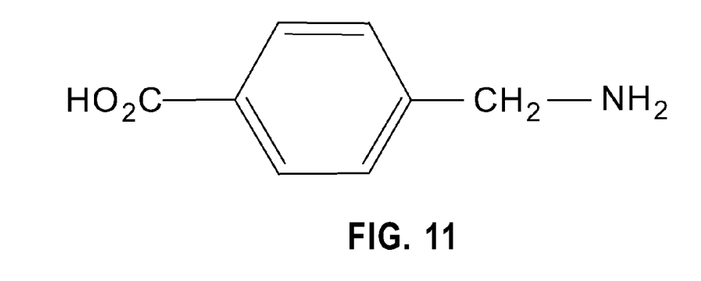
FIG. 11 is the chemical structure of 4-aminomethylbenzoic acid according to the second embodiment of the present invention.

A solution of 2-nitrobenzyloxycarbonyl chloride in anhydrous ether is added to a solution of 4-aminomethylbenzoic acid in lithium hydroxide. For example, 5 mmole of 2-nitrobenzyloxycarbonyl chloride in 40 ml of anhydrous ether is added with stirring to a solution of 4-aminomethylbenzoic acid in 50 ml of 5% lithium hydroxide. The structural formula for 4-aminomethylbenzoic acid is shown in FIG. 11.

Figure 12:
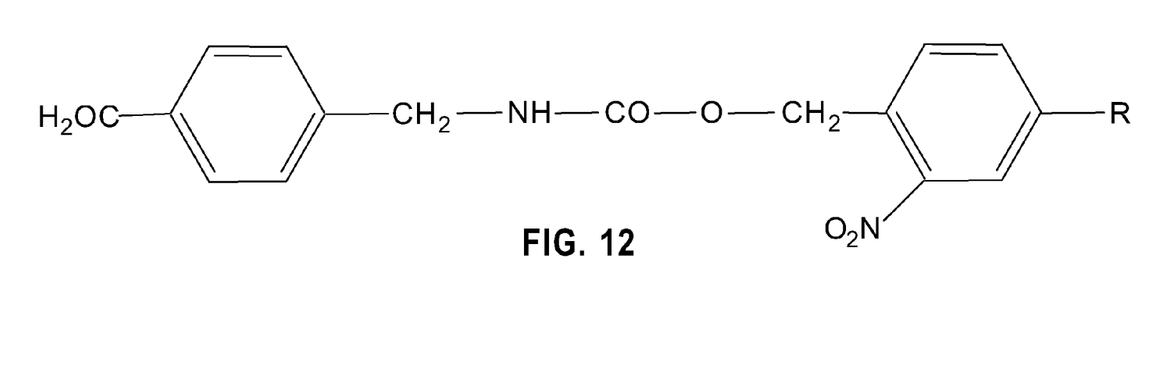
FIG. 12 is the chemical structure of a carbamate according to the second embodiment of the present invention.

The mixture is thereafter stirred, for example, for additional 2 hours. Ether is evaporated and the aqueous solution is acidified with dilute hydrochloric acid. The precipitate is filtered, washed with water, and then dried. Crystallization from ethanol produces a carbamate in the form of white crystals, of which the chemical formula is shown in FIG. 12.

A 2 molar solution of oxalyl chloride in 10 ml dichloromethane is added to a suspension of 10 mmole carbamate in 50 ml of anhydrous dichloromethane containing traces of N,N-dimethylformamide. The solution is stirred for 4 hours, and then the solvent and excess oxalyl chloride is evaporated under reduced pressure. An oily residue therefrom is dissolved in anhydrous 20 ml of dichloromethane, and added to a solution of O-trimethylsilylhydroxylamine (12 mmole) and triethylamine (20 mmole) in 50 ml of dichloromethane. The solution is then stirred for 2 hours, washed successively with dilute hydrochloric acid and brine, dried over anhydrous magnesium sulfate, and evaporated. The residue is dissolved in 20 ml of methanol, and 1 ml of trifluoroacetic acid is added and stirred for 6 hours. The precipitate is filtered and washed several times with water and then dried. Crystallization from ethanol affords the photosensitive hydroxamic acid.

Figure 13:
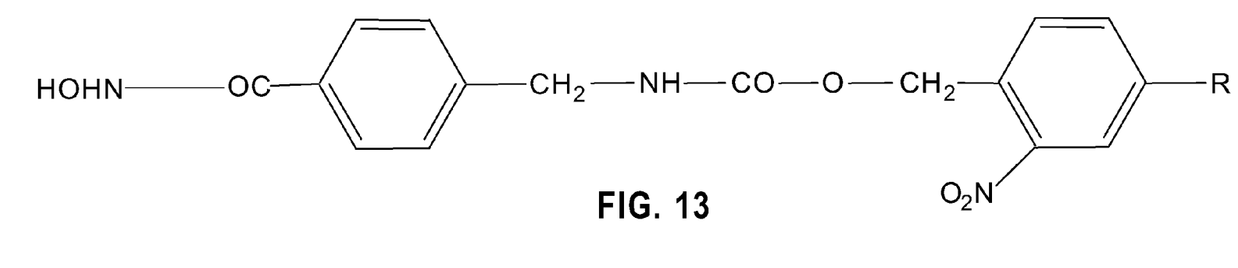
FIG. 13 is the chemical structure of a photosensitive hydroxamic acid according to the second embodiment of the present invention.

The chemical structure of the photosensitive hydroxamic acid is obtained from the chemical structure of FIG. 13 by replacement of R with a hydrogen atom, i.e., by substituting H- for R in FIG. 13.

The above procedure may be performed with the replacement of the 2-nitrobenzyl alcohol with 4-trifluoromethyl-2-nitrobenzyl alcohol. A 4-substituted photosensitive hydroxamic acid, in which R in FIG. 13 is replaced with $CF_3$—, is obtained by this process.

Further, the above procedure may be performed with the replacement of the 2-nitrobenzyl alcohol with 4-hexadecyloxy-2-nitrobenzyl alcohol. Another 4-substituted photosensitive hydroxamic acid, in which R in FIG. 13 is replaced with $C_{16}H_{33}O$—, is obtained by this process.

In general, various alcohol may be employed to produce various photosensitive hydroxamic acid. R may be one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

Figure 14:
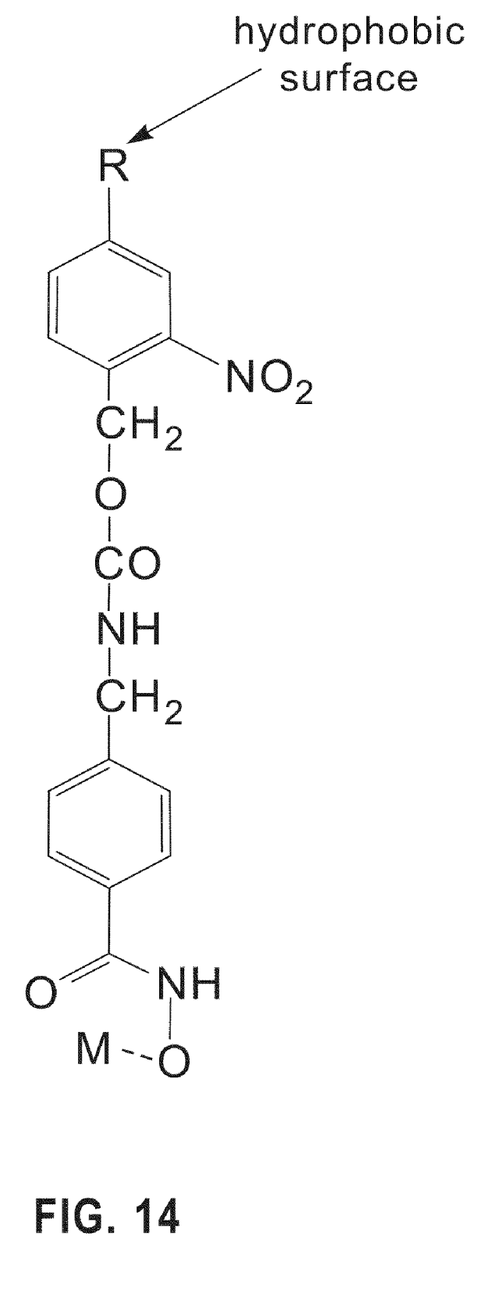
FIG. 14 is the chemical structure of photosensitive hydroxamic acid as attached to an oxide surface according to the first embodiment of the present invention.

Referring to FIG. 14, an unsubstituted or 4-substituted photosensitive hydroxamic acid as covalently bonded to a metal M on the surface of a metal oxide is shown. Two oxygen atoms bond to the metal oxide and provide a hydrophobic surface as R is exposed on the outside of the monolayer 200 (See FIG. 1). The end group of the unsubstituted or 4-substituted photosensitive hydroxamic acid has the formula CONHOH. During bonding to the oxide surface, the end group loses a hydrogen atom. Thus, an oxygen atoms form a covalent bond with the metal atom or the semiconductor atom of the oxide on the surface.

Figure 15:
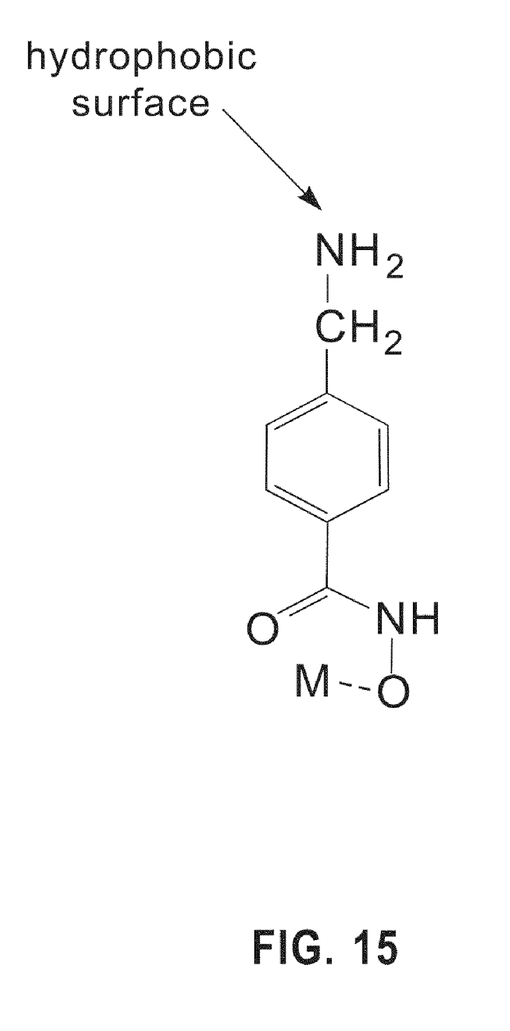
FIG. 15 is the chemical structure of a derivative of the photosensitive hydroxamic acid upon exposure to ultraviolet radiation to form a hydrophilic surface containing an amine end group and as attached to an oxide surface according to the first embodiment of the present invention.

Referring to FIG. 15, a derivative of the unsubstituted or 4-substituted photosensitive hydroxamic acid after exposure to ultraviolet radiation is shown in which the $CH_2$—NH—CO bond in the photosensitive hydroxamic acid is broken to provide a $CH_2$—$NH_2$ termination, which provides hydrophilicity. Thus, the derivative of the photosensitive hydroxamic acid as covalently bonded to the metal M on the surface of the metal oxide provides a hydrophilic surface since —OH is exposed on the outside of the second contiguous region 320 of the monolayer 200.

Examples of Self-assembly and Photopatterning

Example I

Figure 16A:
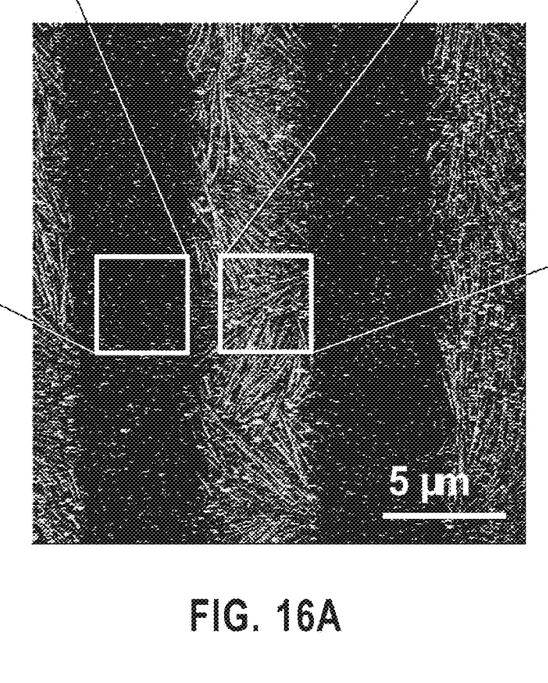
FIG. 16A is an atomic force micrograph of a lithographically ultraviolet radiation exposed sample containing a monolayer of photosensitive phosphonic acid.
Figure 16B:
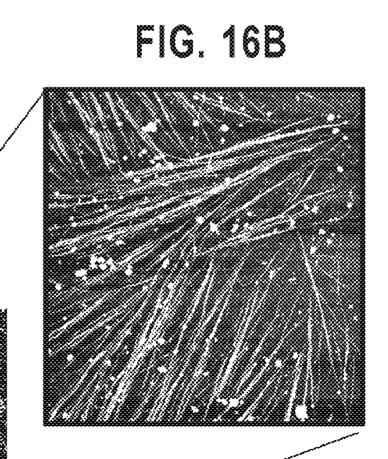
FIG. 16B is a magnified view of an exposed region showing presence of carbon nanotubes therein.
Figure 16C:
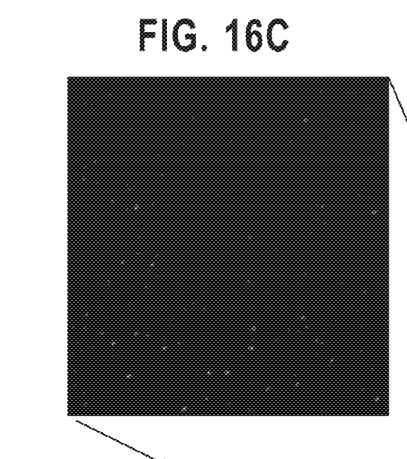
FIG. 16C is a magnified view of a masked region showing absence of any carbon nanotubes therein.

A silicon substrate with 10 nm of hafnium oxide was cleaned by oxygen plasma and immersed in a 1 mmolar solution of unsubstituted photosensitive phosphonic acid in ethanol. After 4 hours, the sample was removed and washed with ethanol and dried. Contact angle measurement showed a contact angle of average 80 degree with water. The sample was then exposed to ultraviolet light of 254 nm wavelength for half an hour and washed with ethanol and dried with stream of nitrogen. The contact angle had changed to average of 20 degree. The sample was immersed in an aqueous dispersion of CNTs in 1% sodium dodecyl sulfonate and dried. An atomic force micrograph of the ultraviolet-exposed sample, as shown in FIG. 16A, shows relatively high density of carbon nanotubes on the surface, whereas an atomic force micrograph of the unexposed sample, as shown in FIG. 16B, does not contain any carbon nanotube.

Example II

Figure 17A:
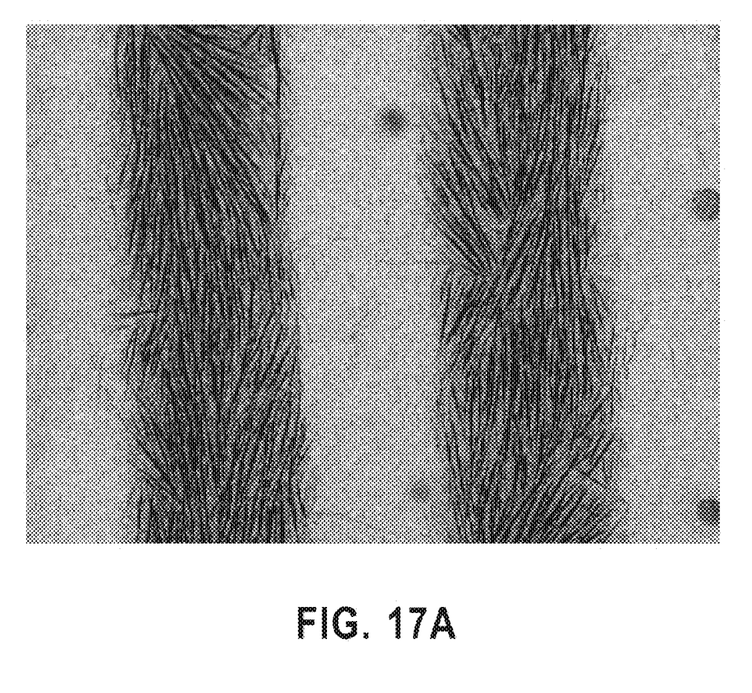
FIGS. 17A and 17B are scanning electron micrographs of functionalized functionalized carbon nanotubes deposited on a photosensitive monolayer of 4-trifluoromethyl photosensitive phosphonic acid, which was patterned by selective ultraviolet irradiation.
Figure 17B:
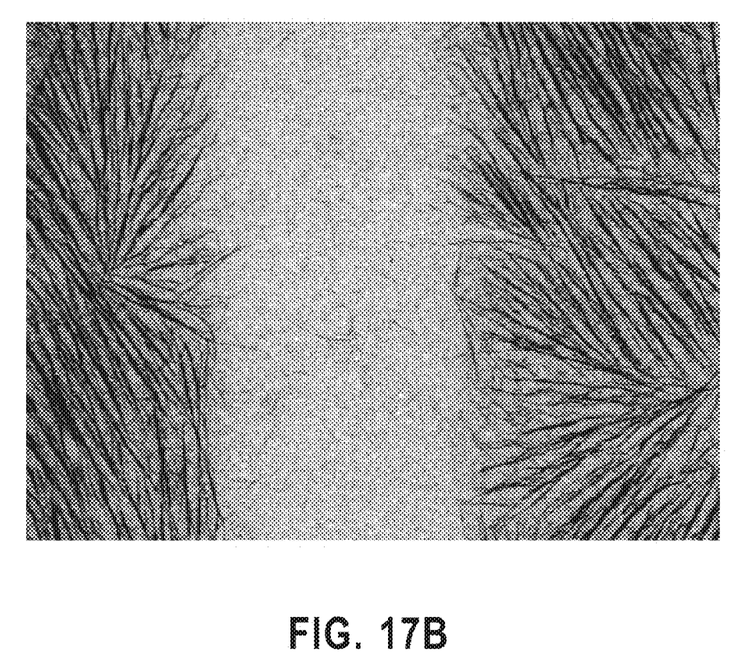

Selective placement of carbon nanotubes (CNTs) was demonstrated in another test. A silicon wafer coated with 10 nm of hafnium oxide was cleaned with oxygen plasma and then immersed in a 1 mmolar solution of 4-trifluoromethly photosensitive phosphonic acid in ethanol for 4 hours. The sample was removed and washed with ethanol and dried under stream of nitrogen. The sample was then exposed through a mask with 5 micrometer pitch to ultraviolet light for half an hour. After rinsing with ethanol, a solution of hydroxamic acid-functionalized carbon nantubes in methanol was drop cast on the sample, dried, and then rinsed with methanol. Carbon nanotubes were selectively placed on the exposed areas of the monolayer. Scanning electron micrographs shown in FIGS. 17A and 17B revealed that the monolayer was patterned with 5 micrometer lines, in which the carbon nanotubes are preferentially attached to the exposed region, while the center of the unexposed regions are free of carbon nanotubes.

Example III

A silicon wafer with 10 nm of hafnium oxide was cleaned by oxygen plasma and then immersed in a 0.5 mmolar solution of 4-trifluoromethly photosensitive phosphonic acid for 8 hours. The sample was removed, washed with and ethanol successively, and dried by slow stream of nitrogen. The sample was exposed through a mask with 5 micrometer pitch to 254 nm ultraviolet radiation for 30 minutes. After the exposure, the sample was washed with chloroform and ethanol successively, and dried under nitrogen.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A photosensitive compound of the structural formula wherein R is one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

2. A photosensitive compound of the structural formula wherein R is one of hydrogen, fully or partially fluorinated alkyl, fully or partially fluorinated alkoxy, or fully or partially fluorinated alkylthio, and wherein a total number of carbon atoms in said alkyl, alkoxy, or said alkylthio is from 1 to 20.

* * * * *